United States Patent [19]

Klawatter

[11] 4,308,624
[45] Jan. 5, 1982

[54] HEART VALVE PROSTHESIS

[75] Inventor: Jerome J. Klawatter, New Orleans, La.

[73] Assignee: Hemex, Inc., Austin, Tex.

[21] Appl. No.: 64,401

[22] Filed: Aug. 7, 1979

[51] Int. Cl.³ .............................................. A61F 1/22
[52] U.S. Cl. ...................................... 3/1.5; 137/512.1; 137/527.8
[58] Field of Search ................... 3/1.5; 137/512.1, 527, 137/527.8

[56] References Cited

U.S. PATENT DOCUMENTS

| | | | |
|---|---|---|---|
| 3,448,465 | 6/1969 | Pierce et al. | 3/1.5 |
| 3,546,711 | 12/1970 | Bokros | 3/1.5 |
| 3,589,392 | 6/1971 | Meyer | 3/1.5 X |
| 3,903,548 | 9/1975 | Nakib | 3/1.5 |
| 3,926,215 | 12/1975 | Macleod | 3/1.5 X |
| 4,078,268 | 3/1978 | Possis | 3/1.5 |
| 4,159,543 | 7/1979 | Carpentier | 3/1.5 |
| 4,178,639 | 12/1979 | Bokros | 3/1.5 |
| 4,225,980 | 10/1980 | Martinez | 3/1.5 |
| 4,263,680 | 4/1981 | Reul et al. | 3/1.5 |

FOREIGN PATENT DOCUMENTS

| | | | |
|---|---|---|---|
| 2753159 | 5/1979 | Fed. Rep. of Germany | 3/1.5 |
| 1160008 | 7/1969 | United Kingdom | 3/1.5 |

*Primary Examiner*—Ronald L. Frinks
*Attorney, Agent, or Firm*—Fitch, Even, Tabin, Flannery & Welsh

[57] ABSTRACT

Single or double-leaflet heart valves include leaflet valve members which are arcuate in cross section, preferably being essentially a portion of the wall of a circular tube. Generally spherical sectors protrude oppositely from the leaflets and are received in elongated, complementary depressions in the interior wall of the annular valve body at generally diametrically opposite locations. As the leaflets pivot between the open and closed positions, the guides move from one end of the elongated depressions to the other. Eccentric pivot axes provide for quick response of the leaflets, and their arcuate shape coupled with shifting of the axes during pivoting moves the leaflets out of the center of the valve passageway reducing resistance to the free flow of blood.

19 Claims, 11 Drawing Figures

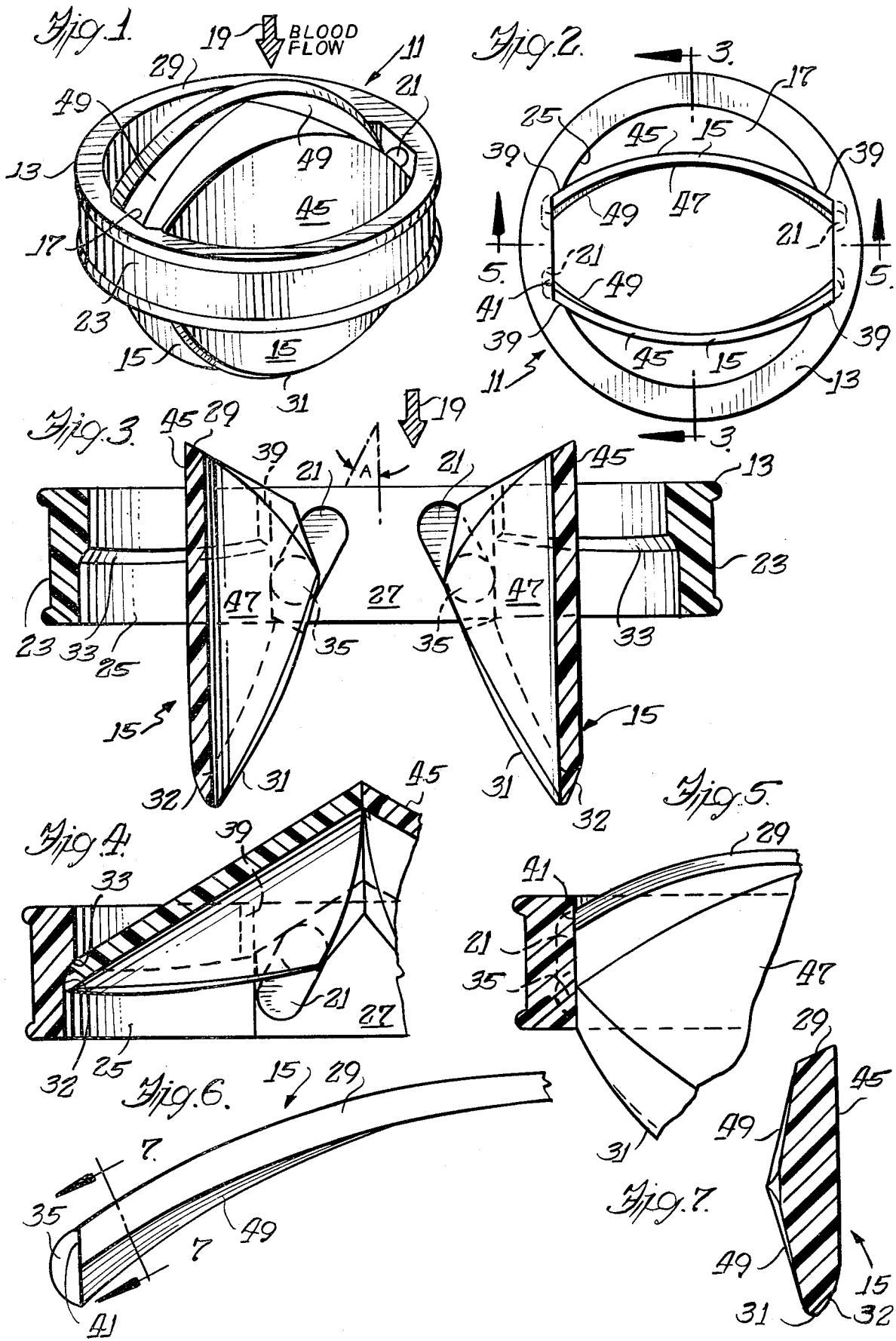

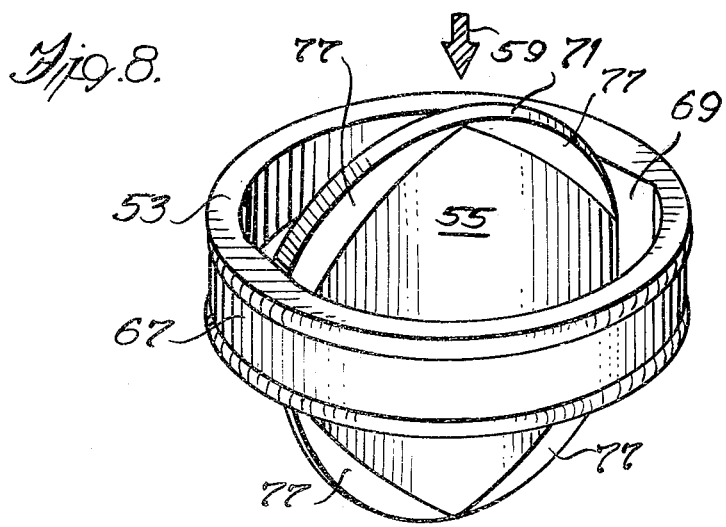
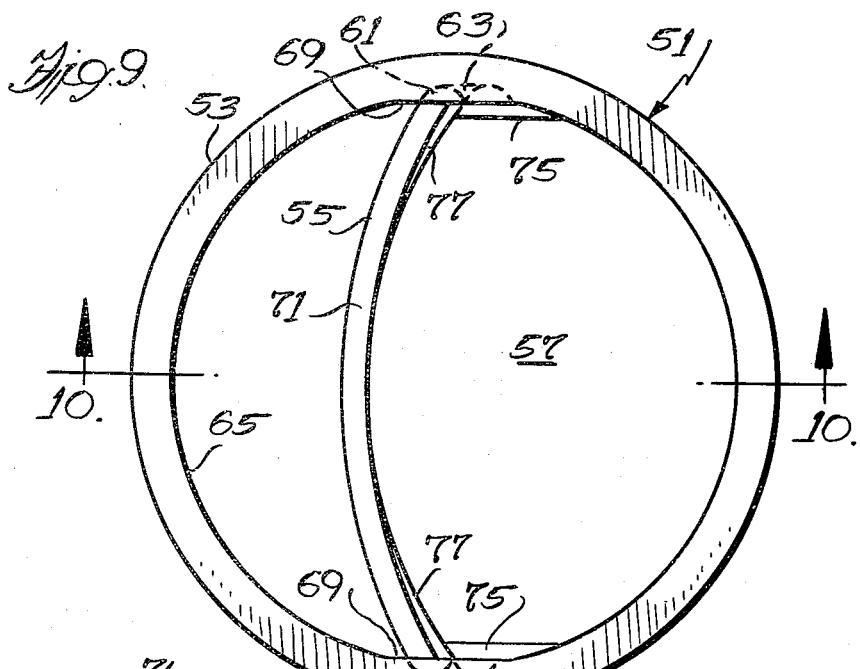
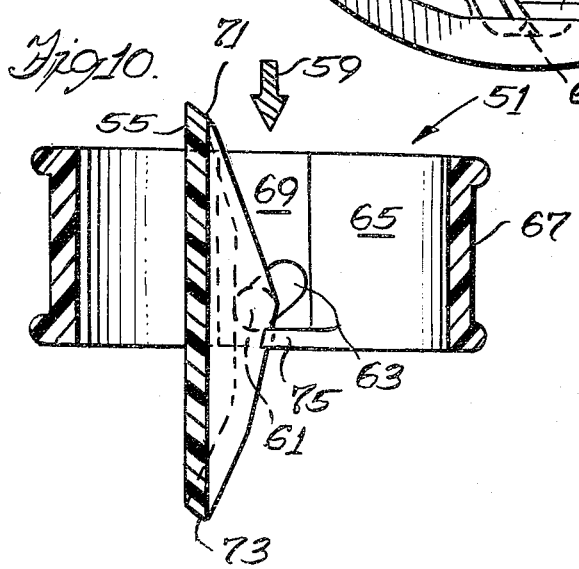
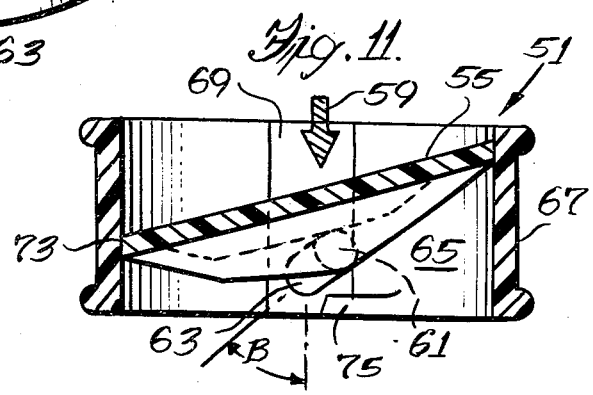

HEART VALVE PROSTHESIS

BACKGROUND OF THE INVENTION

This invention relates to heart valve prostheses for replacement of defective natural valves and more particularly to heart valve prostheses using one or more pivoting valve members which are arcuate in cross section.

Various types of heart valve prostheses have been developed which operate hemodynamically as a result of the pumping action of the heart. Some of these valves which have been used employ a ball-and-cage arrangement, whereas others have used a disc-type arrangement for the valve member. Exemplary of a disc of the free floating type is U.S. Pat. No. 3,534,411, issued Oct. 20, 1970. Various disc-type valves having a pivotal arrangement have been developed, such as that shown in U.S. Pat. No. 3,546,711 to Bokros, issued Dec. 15, 1970, and that shown in U.S. Pat. No. 3,859,668, issued Jan. 14, 1975.

Disc-type heart valves have also been developed which use two members or leaflets, instead of a single disc, which leaflets rotate about parallel axes as a part of the opening and closing of the valve. British Pat. No. 1,160,008 shows an early version of such a valve, and U.S. Pat. No. 4,078,268, issued Mar. 14, 1978, shows a later version.

The present invention includes both a single-leaf and a two-leaflet heart valve prosthesis.

SUMMARY OF THE INVENTION

The invention provides an improved version of a two-leaflet heart valve prosthesis based upon a concept that also provides an improved single leaf heart valve. Guides extend from opposite sides of the single leaf valve member or from each of the leaflets and are received in elongated depressions or grooves formed in the walls of an annular valve body. The valve members are curved in cross section, and each pivots about a changing axis and this movement in the depressions prevents blood clotting from beginning in an otherwise stagnant region. The arcuate shape of the valve members provides a large central passageway for blood flow therethrough. The heart valves open and close easily and reliably and exhibit excellent resistance to wear because of its design.

IN THE DRAWINGS

FIG. 1 is a perspective view of a heart valve embodying various features of the invention and having a pair of leaflets which are shown in the open position;

FIG. 2 is a plan view of the valve of FIG. 1 shown in the open position;

FIGS. 3 and 4 are enlarged sectional views taken along the line 3—3 of FIG. 2, showing the valve in the open and closed positions;

FIG. 5 is an enlarged fragmentary sectional view taken generally along the line 5—5 of FIG. 2;

FIG. 6 is a fragmentary plan view of one of the leaflets of the valve of FIG. 1;

FIG. 7 is a sectional view taken along the line 7—7 of FIG. 6;

FIG. 8 is a perspective view of a heart valve similar to that shown in FIG. 1 but utilizing a single leaf valve member;

FIG. 9 is a plan view of the valve shown in FIG. 8; and

FIGS. 10 and 11 are enlarged sectional views taken along line 10—10 of FIG. 9 showing the valve in the open and closed positions, respectively.

DETAILED DESCRIPTION OF THE PREFERRED EMBODIMENT

Illustrated in FIG. 1 is a heart valve 11 which has an annular valve body or housing 13 which carries a pair of pivoting leaflets or valve members 15 which open and close to control the flow of blood through a central passageway 17 in the direction of the arrow 19 (FIG. 2). The leaflets 15 are supported about eccentric axes in generally diametrically opposed depressions 21 formed within the annular valve body 13. Of course, the valve 11 can operate in any orientation and is not significantly affected by gravity; however, for ease of explanation, the valve 11 is shown and described with the annular valve body 13 being disposed horizontally.

The valve body 13 is formed with a peripheral groove 23 about its exterior surface that accommodates a suturing ring (not shown) which may be of any of the various types already well-known in the art. The suturing ring facilitates the sewing or suturing of the heart valve 11 to the heart tissue.

The passageway 17 through the valve body 13 is generally circular in cross section, and an internal wall 25 of the valve body which defines the passageway 17 preferably has the overall shape of the surface of a hollow right circular cylinder. However, the elongated depressions 21 are formed in flat or planar section 27 of the internal wall 25, and in this respect the passageway deviates slightly from being perfectly circular in cross section.

The valve body 13 and the leaflets 15 are made of suitable material that is biocompatible and nonthrombogenic and that will take the wear to which it will be subjected during countless openings and closings of the leaflets. Preferably, the components are made from isotropic polycrystalline graphite, such as that sold under the tradename POCO, which has been suitably coated with pyrolytic carbon, such as that marketed under the trademark PYROLITE, which gives excellent compatibility and wear-resistance.

The leaflets 15 are arcuate in transverse cross section and may have a nominally uniform thickness along the upstream and downstream edges, as best seen in FIG. 2. They have the general shape of a section of a tube of circular cross section. A minor edge 29 (which is the upstream edge of the leaflet 15 with respect to normal blood flow through the valve) is planar and a major edge 31 (which faces downstream in the open position) has the general shape of a portion of an ellipse to match the line along which it meets the inner surface of the generally cylindrical passageway 17. The outline of the arcuate major edge 31 is generally defined by the intersection between a circular cross section tubular section and the right cylindrical interior wall surface 25 of the valve body 13. The minor 29 and major 31 edges of the leaflets 15 are preferably appropriately shaped so that, in the closed position of the valve 11, the upper or upstream surface 32 of the major arcuate edge 31 fits against an appropriately rounded undersurface of a seat 33 which protrudes inwardly from the interior wall 25 and so that the minor planar edge surface 29 of one leaflet abuts against the similar planar edge surface of the other leaflet.

The pivotal axis for each of the leaflets 15 is eccentric to the leaflet and also to the centerline through the valve passageway 17, and it is defined by the location of a pair of oppositely extending guides 35 which are preferably spherical sectors. A spherical sector is that part of a sphere which is formed by a plane cutting the sphere, and the diameter of the sector is the diameter of the circle of intersection. The guides 35 are formed at opposite lateral locations on the arcuate leaflets 15 and are accommodated within elongated depressions or grooves 21 which have a radius of curvature, at the ends thereof, equal to or slightly larger than that of the spherical guides. The cross sections of the elongated depressions 21 have a similar radius of curvature that facilitates the pivotal and longitudinal movement of the guides. The leaflets 15 are each installed in the valve body 13 so their concave surface faces the centerline of the passageway 17 when in the open position (see FIG. 2).

The elongated depressions 21 are aligned somewhere between the vertical (i.e., parallel to the axis of the passageway 17) and at an angle A (FIG. 3) of not more than about 60° thereto extending outward in the downstream direction of blood flow. In the illustrated valve angle A is equal to about 30°. The distance between the bottoms of the elongated concave surfaces of the depressions 21 is just slightly longer than the distance between the ends of the convex spherical surfaces of the guides 35, which provides sufficient clearance so the guides 35 can pivot and move freely therein. The material from which the valve body 13 and leaflets are made has sufficient resiliency to allow the leaflets 15 to be snapped into operative position with the guides 35 received in the elongated depressions 21.

Each depression 21 preferably has a total length which is at least about 125 percent of the diameter of the spherical sector of the guides so that the movement of the guides 35 within the depressions coupled with the flow of blood therepast washes the entire concave surface of the depressions so that a positive deterent to clotting is provided. Although a longer depression could be used, the illustrated depressions 21 having a length equal to about twice the diameter of the sector is most adequate for this purpose. To assure freedom of movement, the radii of curvature of the opposite ends of the depression 21 are preferably slightly greater than the radius of curvature of the guides 35.

The minor planar edges 29 abut and may serve as a stop when the leaflets reach the closed position; however, the primary stop is preferably provided where the arcuate downstream edges 31 of the leaflets abut the interior wall 23 of the valve body. A pair of arcuate stops or seats 33 are preferably formed in the interior valve wall 25 and engage with the upper surface 32 of the generally elliptical edge 31 along substantially its entire length. The lateral edges of the stops 33 are cut so as to serve as stops 39 for the leaflets in the open position as best seen in FIG. 2. The stops 39 are preferably located to position the leaflets with their axes parallel to the axis of the central passageway 17 where they exert the least resistance to blood flow; however, the axes may be tilted slightly, i.e., about 10° in either direction. Even though the leaflets, in the open position, are oriented parallel to the axis of the passageway, when blood flow through the heart chamber changes direction, the back pressure causes a backflow of the blood which exerts a dragging force on the curved leaflets 15 that is amplified by the composite moment arm (by which the major surface portion of the leaflet is offset from the pivotal axis of the leaflet) and quickly closes the valve 11.

Depending upon the proportioning and the location of the protruding stop 33, each leaflet 15 may pivot between about 55° and 65° in moving between its vertical orientation in the open position and the orientation in the closed position shown in FIG. 4. One example of a heart valve 11 designed for aortic location may have an outer diameter of about 24 millimeters and a central passageway 17 of about 21 millimeters in general diameter. The spherical guides 35 may extend about 2½ millimeters outward from the otherwise planar surfaces 41 on the opposite lateral sides of the leaflet, as best seen in FIG. 5. The central portion of the curved leaflet 15 may have a thickness of about ¾ millimeter.

In the open position illustrated in FIG. 3, each leaflet 15 has swung downward to a position where the axis of its outward facing convex surface is parallel to the centerline of the passageway 17, and in this position the guides 35 have moved to the lower rounded ends of the depressions 21. During the opening movement of the leaflets 15, blood is flowing through the valve 11 in the direction of the arrow 19 on the pumping stroke of the heart as a respective ventricle contracts. Pivoting movement is halted when the outward facing surfaces of the leaflets contact the stops 39; however, because the tendency of blood flow is such to inherently orient the leaflets in a vertical position, there is very little pressure exerted against the stops 39 and wear is not a problem. Because of their arcuate cross sectional shape and because the leaflets 15 have moved outward from the center as a result of the angle of orientation of the elongated depressions 21, the main central passageway between the leaflets is quite large in size (see FIG. 2) and allows free flow of blood therethrough. In this respect the radius of the tubular section which constitutes the leaflet 15 (measured from the midpoint between the surfaces) should be equal to between about 125 percent and about 200 percent of the radius of the passageway 17 to provide such clearance along the centerline in the open position.

At the end of the stroke, the respective ventricle relaxes to draw more blood into the chamber from the atrium, and the back pressure within the left aorta causes the leaflets 15 to quickly swing or pivot to the closed position depicted in FIG. 4. Each leaflet 15 pivots about an axis which is defined by the spherical sector guides 35, and its construction is such that the drag of blood flow along the leaflet surface creates a force which acts through a significant moment arm causing a very prompt closing response. In the closing movement of the leaflets 15, the guides 35 move upward and inward in the depressions 21, while pivoting about the guides is occurring, until the elliptical major edge 31 of each leaflet 15 contacts the interior side wall 25 of the passageway 17. At this point, the planar minor edge surfaces 29 of the leaflets 15 come in contact with each other, closing the passageway 17 to blood flow.

The upper surface 32 of the elliptical edge 31 is rounded and matched to the radius of curvature of the underside of the seat 33 to assure a good seal occurs at this point. The leaflets 15 are preferably proportioned so that, when sealing contact has been established both along the abutting edge surfaces 29 and between the edge surfaces 32 and the seats 33, the guides 35 are displaced just slightly from the rounded upper ends of the depressions 21, thus lessening wear in this region.

As best seen from FIGS. 2, 5 and 6, the interior planar wall sections 27 of the valve body lie in close proximity to flat regions 41 formed on opposite lateral edges of the leaflets 15 in surrounding location to the guides 35. This proportioning of the leaflets 15 assures that the flat surfaces 41 move closely adjacent to the interior planar wall sections 27 as the leaflets pivot, and the arrangement provides adequate sealing in these diametrically opposite regions.

The curved leaflets 15 have a shape which generally resembles a section of a tube of circular cross section or a hollow right circular cylinder. In the preferred construction illustrated in the drawings, it is machined from a single piece of material, preferably polycrystalline graphite, and as a result does not have a uniform thickness. As best seen in FIG. 2, the outward facing surface 45 of the leaflet 15 is that of a convex, right circular cylindrical surface, and the original piece of material from which the leaflet is machined has a concave surface of a right circular cylinder of lesser radius. In the manufacturing process, the guides 35 are formed as sectors of a sphere of a desired radius at the appropriate aligned locations at the opposite lateral sides of each leaflet and thus define the eccentric axis about which the guide pivots. The guides 35 need not be an entire hemisphere but may be a spherical sector having a depth equal to about half the radius of the sphere. Likewise, the guides could be a sector of some other, generally spherical, surface of revolution, such as a paraboloid, a hyperboloid, or an ellipsoid. However, it is easiest to machine a spherical sector, and use of a spherical sector is preferred.

Following the machining of the spherical sector guides 35, the machining of the flat regions 41 surrounding the guides on the opposite lateral sides of the leaflets 15 is completed. Chamfering of the concave surface 47 of the leaflets is then carried out at four locations so as to remove material from the leaflet which is not needed for strength—thus rendering the leaflets lower in mass and more responsive to opening and closing forces. Four chamfers 49 are effected beginning at the lateral edges at the level of the centerline of the guides and extending toward the center and either upward to the minor planar edge 29 of the leaflet or downward to the major elliptical edge 31. As a result of the chamfers 49, the top and bottom edges of the leaflets are of uniform thickness, as best seen along the top edge in FIG. 2. After the entire machining process has been completed, the polycrystalline graphite leaflet substrate is coated with PYROLITE pyrolytic carbon to provide an integral, strong, wear-resistant, biocompatible surface about the entire exterior of the leaflet.

As best seen in FIGS. 3 and 4, the convex surface of each leaflet 15 is rounded at its elliptical major edge 31 to provide the narrow surface region 32 which extends from the flat region 41 on one side to the flat region 41 on the other side. The underside of the stop 33 protruding from the valve body wall 25 is formed with a concave surface of complementary curvature so as to provide surface-to-surface contact over its entire length—thus achieving an excellent seal against blood flow.

The elongated depressions 21 wherein the guides 35 travel have rounded ends which have a radius of curvature equal to or up to about 5 percent greater than the radius of curvature of the spherical guides, and preferably the radius of curvature is between about 1 and about 3 percent greater. The width of the depressions 21 is similarly between about 1 and about 3 percent greater than the diameter of the spherical sector. The total length of the illustrated depressions 21 is equal to about twice the diameter of the spherical sector guide, and in general its length is preferably between about 150 percent and about 225 percent of the sector diameter. It is important that the depressions 21 are elongated so that there is movement of the guides 35 back and forth therealong to prevent any stagnant region of blood from accumulating that could be the beginning of a clot, and as previously mentioned, the total length of the depression should be at least about 125 percent of the sector diameter.

In the illustrated embodiment, as best seen in FIG. 3, the elongated depressions 21 are aligned at an angle of 30° to the vertical plane passing through the centerline of the valve passageway which is parallel to the eccentric axes of the leaflets. Because this angle A may be between 0° and about 45°, the elongated depressions 21 can be aligned either vertical (i.e., directly downstream of normal blood flow) or at an angle downstream and laterally toward the side of the valve body toward which the leaflet is pivoting. Preferably, the angle is at least about 20°, and the effect of the angle can be seen by comparing FIGS. 3 and 4. During opening movement, the leaflets move further outward from the center of the passageway 17 as they pivot into a vertical orientation, thus providing a very large, central passageway through the valve as depicted in FIG. 2. Inasmuch as the major portion of the blood flows through the central portion of the passageway, it can be seen that the valve 11 will exhibit excellent flow properties.

It can particularly be seen from FIGS. 3 and 4, that the valve body 13 has a very low profile, and this is considered to be a significant advantage in heart valve construction. It not only facilitates machining of the valve components, but it facilitates placement of the valve in the heart of the recipient.

Illustrated in FIGS. 8 through 10 is a heart valve 51 which includes an annular valve body or housing 53 and a single valve member or leaf 55. The leaf 55 pivots to open and close a central passageway 57 formed by the annular valve body through which blood in the normal course flows downward as indicated by the arrow 59. The leaflet 55 is supported about an eccentric axis by a pair of guides 61 which protrude outward therefrom in opposite directions and which are received in generally diametrically opposed depressions 63 formed in the interior wall 65 of the annular valve body.

The valve 51 can operate in any orientation and is not significantly affected by gravity; however, for ease of explanation and consistency with the illustration of the valve 11, the valve 51 is shown and described with the annular valve body disposed horizontally and with normal blood flow being vertically downward therethrough. The valve body 53 is also formed with a peripheral groove 67 which accommodates a suturing ring.

The passageway 57 through the annular valve body 53 is substantially circular in cross section and is defined by the interior valve wall 65 which has the general shape of a surface of a hollow, right circular cylinder. Preferably however, the elongated depressions 63 are formed in flat or planar sections 69 of the internal wall 65, and in this respect the passageway 57 deviates slightly from being perfectly circular in cross section. The valve body 53 and leaflet 55 are formed of the same material as in the heart valve 11.

The leaf 55 is arcuate in transverse cross section and preferably has a nominally uniform thickness along its upstream and downstream edges 71 and 73, respectively, as best seen in FIGS. 9 and 10. Overall, the leaf valve member 55 has the general shape of a section of a tube of circular cross section, with the guides 61 extending outward from the lateral edges of this tubular section. The transverse pivot axis is according to the axis of the leaf which extends in the longitudinal direction.

As best seen in FIG. 11, the upstream edge 71 and the downstream edge 73 of the leaf are about the same length. The shape of both edges is accordingly defined by the intersection between a pair of hollow, right circular cylinders of different diameters. However, the arcuate orientation of the edges 71 and 73 is such that both edges smoothly and closely abut the internal cylindrical wall 65 of the annular valve body 53 and seal the passageway through the valve in the closed position, illustrated in FIG. 11.

The eccentric pivotal axis of the leaf valve member 55 is defined by the oppositely extending guides 61 which, as in the case of the heart valve 11, are generally spherical in shape and are preferably spherical sectors. The criteria of the elongated depressions or grooves 63 are the same as indicated with respect to the depressions 21, from a proportioning standpoint. The depressions extend in a straight line which is again equal to about 125 percent of the diameter of the sector and which in the illustrated embodiment is about 200 percent thereof. Preferably, the length of the depressions is equal to between about 150 and 225 percent of the sector diameter.

The direction along which the depressions 63 extend is preferably at an angle of between about 20° and about 60° to the plane extending through the centerline of the valve, or to a plane parallel therewith. This angle is marked "B" in FIG. 11. The direction of the angle is again such that the major portion of the valve member 55 moves radially outward in the passageway 57 as it is pivoting to the open position. This movement plus the arcuate cross sectional shape of the valve member 55 opens up the center of the passageway 57 for normal blood flow therethrough, as best seen in FIG. 9.

Preferably, a pair of stops 75 are provided which protrude out from the flat sections 69 of the valve body to position the single valve member 55 in the open position wherein it is aligned parallel to the centerline of the valve passageway and thus presents minimum resistance to flow therethrough. Although, as earlier indicated, it would be acceptable for the valve member 55 to be tilted up to about 10° in either direction from this alignment. As best seen in FIG. 9, the stops 75 are shaped along their inward edges to match the shape of the edge of the leaf 55 with which contact will be made, whereas the opposite edge of each stop flares smoothly into the interior wall 65 of the valve body. However, it might be preferable to slightly blunt the edge of the valve member in this region and to change the shape of the stops 75 correspondingly to thicken the region of the valve member where contact will occur, even though the contact force is not great inasmuch as the valve member in this position is aligned with the flow of the blood stream through the passageway.

In the open position shown in FIG. 10, the leaf 55 has swung downward so that the axis of the leaf, which is essentially a section of a circular tube, is parallel to the centerline of the passageway 57. In this position, it can be seen that the guides 55 reside in the lower ends of the depressions 63 and that the valve member is held against any further counterclockwise pivoting movement by the stops 75. From FIG. 9, it can be seen that the arcuate nature of the valve member 55 displaces it substantially from the centerline of the valve in the open position, thus vacating the center of the passageway 57 for free flow of blood therethrough. In this respect, the radius of the tubular section which constitutes the leaf 55 (measured from the midpoint between its outward-facing convex surface and its inward-facing concave surface) should be equal to between about 125 percent and about 200 percent of the radius of the passageway 57.

At the end of this pumping stroke which causes blood to flow through the open valve 51, the respective ventricle relaxes to draw more blood into the chamber from the atrium, and the back pressure of blood from the left aorta causes the leaf 55 to quickly swing or pivot to the closed position depicted in FIG. 11. In the orientation as shown in the drawings, the valve member 55 swings about 67° in a clockwise direction to reach the fully closed position, and preferably in a single-leaf valve design, pivoting movement is between about 60° and 75°. The closing movement is of course caused by the back pressure of blood which attempts to cause a backflow of blood through the valve; however, the drag of the flowing blood on the convex and concave surfaces of the leaf 55 causes a closing force that is amplified by the composite moment arm (by which the major surface portions of the leaf are offset from its pivotal axis), which effects a prompt clockwise swinging of the leaf. By comparing FIGS. 10 and 11, it can be seen that the guides 63 move from the lower end to the upper end of the depressions 63 during the closing movement to prevent any stagnant region of blood from accumulating at these locations. Machining of the leaf 55 is preferably performed as explained hereinbefore and likewise provides chamfered regions 77 on the concave surface of the leaf.

Although the invention has been described with regard to preferred embodiments which constitute the best mode presently known to the inventor, it should be understood that changes and modifications as would be obvious to one having the ordinary skill in this art may be made without departing from the scope of the invention which is defined solely by the appended claims. For example, the elongated depressions need not extend in a straight direction but could extend along an arcuate path. Various features of the invention are emphasized in the claims which follow.

What is claimed is:

1. A heart valve prosthesis comprising an annular valve body having a central passageway for the flow of blood therethrough in a predetermined direction from upstream to downstream and valve member means which is generally a section of a tube arcuate in transverse cross section having concave and convex surfaces and supported for substantially pivotal movement on eccentric axis means between a closed position blocking blood flow through said central passageway and an open position allowing blood flow therethrough, the convex surface thereof facing upstream in said closed position, said valve member means including a pair of guides projecting in opposite directions which define the pivotal axis thereof, said annular valve body having elongated depressions formed therein at generally diametrically opposite locations wherein said guides are received, each of said elongated depressions extending for a longitudinal distance greater than its transverse dimension so that said guides move back and forth therealong at the same time they move pivotally therewithin thereby defining a shifting pivot axis relative to said valve body as said valve member means pivots from the closed to the open position wherein said concave surface thereof faces the centerline of said central passageway with the longitudinal axis of said tubular section being generally aligned with said passageway centerline and thereby opens up the center for normal blood flow therethrough.

2. A heart valve in accordance with claim 1 wherein said valve member means includes two leaflets which are pivotally supported in pairs of elongated depressions and which together block blood flow through said central passageway.

3. A heart valve in accordance with claim 2 wherein said guides have a radius of curvature and said depressions have rounded ends which have radii of curvature between being equal to up to about 5 percent greater than the radius of said guides.

4. A heart valve in accordance with claim 3 wherein said depressions extend in a substantially straight line.

5. A heart valve in accordance with claim 4 wherein said straight line is oriented at an angle of at least about 20° to the centerline of said passageway.

6. A heart valve in accordance with claim 5 wherein said guides have the shape of generally spherical sectors and wherein said straight line distance is between about 150 percent and about 225 percent of said sector diameter.

7. A heart valve in accordance with claim 6 wherein the radius of curvature of said rounded ends of said depressions is not more than 3 percent greater than the radius of curvature of said spherical sector.

8. A heart valve in accordance with claim 6 wherein said diameter of said spherical sectors is greater than the thickness of a major portion of each leaflet.

9. A heart valve in accordance with claim 2 wherein the valve body has the general shape of a hollow right circular cylinder.

10. A heart valve in accordance with claim 9 wherein each said leaflet has a major peripheral elliptical edge that is contoured to match the contour of the interior wall surface of the hollow cylinder which defines said passageway.

11. A heart valve in accordance with claim 10 wherein a minor peripheral edge surface of each leaflet is planar and wherein said planar surfaces of said leaflet edges abut each other in surface-to-surface contact when said valve leaflets are in the closed position.

12. A heart valve in accordance with claim 9 werein each of said leaflets has the general shape of a section of a tube of circular diameter.

13. A heart valve in accordance with claim 12 wherein each of said leaflets pivots an angle of between about 50° and about 65° between the open position and the closed position.

14. A heart valve in accordance with claim 2 wherein the interior wall of said hollow valve body which defines said central passageway has the general form of a surface of a right circular cylinder and wherein a pair of arcuate stop means protrudes from opposite regions of said valve body wall which stop means seals against abutting edges of each of said leaflets.

15. A heart valve in accordance with claim 14 wherein each of said leaflets has oppositely disposed substantially planar faces from which said guides protrude and wherein the interior wall of said valve body has a pair of substantially planar surface sections which surround said elongated depressions.

16. A heart valve prosthesis comprising an annular valve body having a central passageway for the flow of blood therethrough in a predetermined direction from upstream to downstream and a single valve member which is generally a section of a tube of curved cross section having a concave surface and a convex surface and supported on an eccentric axis for substantially pivotal movement between a closed position blocking blood flow through said central passageway and an open position allowing blood flow therethrough, the convex surface thereof facing upstream in said closed position, said valve member and said annular valve body including interengaging means which define the pivotal axis of said valve member in the form of projecting guides and elongated depressions, with said guides being received within said depressions so that said valve member concave surface faces the centerline of said central passageway in the open position, each of said elongated depressions extending for a longitudinal distance greater than its transverse dimension so that said guides move back and forth therealong at the same time they move pivotally therewithin, and said valve body being formed with stop means for locating said valve member in said open position with the axis of said tube substantially parallel to said passageway centerline.

17. A heart valve in accordance with claim 16 wherein said valve member has the general shape of a section of a tube of circular cross section, wherein said central passageway through said valve body is substantially circular in cross section and wherein the radius of said tube is equal to between about 125 percent and about 200 percent of the radius of said central passageway.

18. A heart valve in accordance with claim 17 wherein said depressions are formed in said valve body and each extends in a substantially straight line.

19. A heart valve in accordance with claim 18 wherein said elongated depressions extend at an angle of at least about 20° to a plane through the passageway centerline so that at least a major portion of said arcuate valve member moves radially outward, during pivoting from the closed position to the open position, relative to the position it would occupy if said depressions extended parallel to said centerline thereby opening the center of the passageway for normal blood flow therethrough.

* * * * *

UNITED STATES PATENT AND TRADEMARK OFFICE
CERTIFICATE OF CORRECTION

PATENT NO. : 4,308,624
DATED : January 5, 1982
INVENTOR(S) : Jerome J. Klawitter It is certified that error appears in the above—identified patent and that said Letters Patent is hereby corrected as shown below:

The inventor's name is Jerome J. Klaw_i_tter, not Klaw_a_tter.

Signed and Sealed this

Fifteenth Day of June 1982

[SEAL]

Attest:

GERALD J. MOSSINGHOFF

Attesting Officer     Commissioner of Patents and Trademarks